United States Patent
Dantzman

(10) Patent No.: US 7,368,448 B2
(45) Date of Patent: May 6, 2008

(54) 2-(ARYLALKOXY)-1-PHENYLETHYLAMINE DERIVATIVES AS NK₁ ANTAGONIST AND SEROTONIN REUPTAKE INHIBITORS

(75) Inventor: Cathy Dantzman, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/599,824

(22) PCT Filed: Apr. 6, 2005

(86) PCT No.: PCT/SE2005/000499

§ 371 (c)(1),
(2), (4) Date: Oct. 11, 2006

(87) PCT Pub. No.: WO2005/100324

PCT Pub. Date: Oct. 27, 2005

(65) Prior Publication Data

US 2007/0185127 A1   Aug. 9, 2007

(30) Foreign Application Priority Data

Apr. 14, 2004   (SE) .................................. 0400968

(51) Int. Cl.
*A61K 31/497* (2006.01)
*C07D 241/04* (2006.01)
*C04D 295/00* (2006.01)
*C07C 211/00* (2006.01)

(52) U.S. Cl. .................. 514/252.12; 544/398; 564/428

(58) Field of Classification Search ................ 564/428; 544/398; 514/252.12
See application file for complete search history.

(56) References Cited

U.S. PATENT DOCUMENTS

| 4,301,163 A | 11/1981 | Torossian et al. |
| 5,245,080 A | 9/1993 | Aubard et al. |
| 5,266,599 A | 11/1993 | Aubard et al. |
| 5,362,756 A | 11/1994 | Riviere et al. |
| 5,389,686 A | 2/1995 | Diop et al. |

FOREIGN PATENT DOCUMENTS

| WO | 94/14767 | * 7/1994 |
| WO | WO 94/14767 | 7/1994 |
| WO | WO 01/46167 | 6/2001 |

OTHER PUBLICATIONS

Ryckmans, et al., Dual NK1 Antagonists—Serotonin Reuptake Inhibitors as Potential Antidepressants. Part 2: SAR and Activity of Benzyloxyphenethyl Piperazine Derivatives, Bioorganic & Medicinal Chemistry Letters, 12, 3195-3198 (2002).*
Genicot, C. et al., "Discovery of orally bioavailable NK1 receptor antagonists"; Bioorg. Med. Chem. Lett. 2003, 13(3), pp. 437-442.
Ryckmans, T. et al., "Dual NK1 antagonists-serotonin reuptake . . . SAR and activity of benzyloxyphenethyl piperazine derivatives"; Bioorg. Med Chem Lett., 2002, 12(21), 3195-3198.

* cited by examiner

*Primary Examiner*—James O. Wilson
*Assistant Examiner*—Erich Lesser
(74) *Attorney, Agent, or Firm*—Pepper Hamilton LLP

(57) ABSTRACT

Compounds of the following formula (I) wherein $R^1$ $R^2$, n, $Ar^1$ and $A^2$ are as defined in the specification, in vivo-hydrolysable precursors thereof, pharmaceutically acceptable salts thereof, the use in therapy and pharmaceutical compositions and methods of treatment using the same. The example compounds are 1-(2-(naphthylmethoxy)-1-phenylethyl)piperazine derivatives. The compounds are neurokinin 1 (NK₁) receptor antagonist and/or serotonin reuptake inhibitors, with medical indications for depression and other disorders

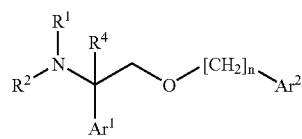

10 Claims, No Drawings

2-(ARYLALKOXY)-1-PHENYLETHYLAMINE DERIVATIVES AS NK₁ ANTAGONIST AND SEROTONIN REUPTAKE INHIBITORS

CROSS-REFERENCE TO RELATED APPLICATIONS

This application is a US National Stage under 35 U.S.C § 371 of International Application No. PCT/SE2005/000499 (filed Apr. 6, 2005) which claims priority under 35 U.S.C § 119 (a)-(d) to Application No. 0400968-4 filed in Sweden on Apr. 14, 2004.

FIELD OF THE INVENTION

This invention relates to the treatment of diseases in which serotonin, Substance P or Neurokinin A are implicated, for example, in the treatment of disorders or conditions such as hypertension, depression, generalized anxiety disorder, phobias, posttraumatic stress syndrome, avoidant personality disorder, premature ejaculation, eating disorders, obesity, chemical dependencies, cluster headache, migraine, pain, Alzheimer's disease, obsessive-compulsive disorder, panic disorder, memory disorders, Parkinson's disease, endocrine disorders vasospasm, cerebellar ataxia, gastrointestinal tract disorders, negative symptoms of schizophrenia, premenstrual syndrome, fibromyalgia syndrome, stress incontinence, Tourette's syndrome, trichotillomania, kleptomania, male impotence, attention deficit hyperactivity disorder, chronic paroxysmal hemicrania and headache.

BACKGROUND

The mammalian neurokinins are peptide neurotransmitters found in the peripheral and central nervous systems. The three principal neurokinins are Substance P (SP), Neurokinin A (NKA) and Neurokinin B (NKB). N-terminally extended forms of at least NKA are known. Three receptor types are known for the principal neurokinins. Based upon their relative selectivities for the neurokinins SP, NKA and NKB, the receptors are classified as neurokinin 1 ($NK_1$), neurokinin 2 ($NK_2$) and neurokinin 3 ($NK_3$) receptors, respectively. In the periphery, SP and NKA are localized in C-afferent sensory neurons, which neurons are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation, increased mucus secretion and activation of mast cells. Neurokinin antagonists that interact with $NK_1$, $NK_2$ and $NK_3$ receptors, having different chemical structures have been described. Particularly international publications WO 98/07722, WO 96/39383 and WO 98/25617, and regional publications EP 428434, EP 474561, EP 515240 and EP 559538 disclose the preparation of a variety of chemical structures.

$NK_1$ activity is also implicated in depression and anxiety, mice with genetically altered $NK_1$ receptors have decreased anxiety related behavior (Santarelli, L., et. al., Proc. Nat. Acad. Sci. (2001), 98, 1912) and $NK_1$ antagonists have been reported to be effective in an animal model of depression (Papp, M., et. al., Behav. Brain Res. (2000), 115, 19).

Selective Serotonin Reuptake Inhibitors (SSRIs) are widely used for the treatment of major depressive disorder (MDD) and are considered well-tolerated and easily administered. SSRIs, however, have a delayed onset of action, are associated with undesirable side effects, such sexual dysfunction, and are ineffective in perhaps 30% of patients (M. J. Gitlin, M J, J. Clin. Psych., 55, 406-413, 1994).

Compounds with dual action as $NK_1$ antagonists and serotonin reuptake inhibitors may also provide a new class of antidepressants. Indeed, compounds combining $NK_1$ antagonism and serotonin reuptake inhibition have been described (Ryckmans, T., et. al, Bioorg. Med. Chem. Lett. (2002), 12, 261).

DESCRIPTION OF THE INVENTION

The present invention encompasses compounds having neurokinin 1 ("$NK_1$") antagonist activity and/or serotonin reuptake inhibitory ("SRI") activity. Aryl glycine compounds of the invention are those on accord with formula I

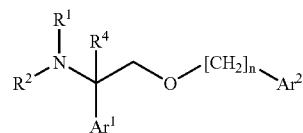

I wherein:

$R^1$ and $R^2$ are independently selected from $C_{1-6}$alkyl or $C_{1-6}$ alkenyl, or together with the N to which they are bound, form a heterocycle containing 6, 7 or 8 atoms or such a heterocycle substituted with moieties independently selected from hydrogen, halogen, $C_{1-4}$alkyl, $C_{1-4}$alkoxy or $C_{1-4}$alkyl substituted with 1, 2 or 3 halo moieties, amino, or amino substituted with $C_{1-4}$alkyl, $C_{1-4}$alkoxy or $C_{1-4}$alkyl, substituted with 0, 1, 2, or 3 halo moieties;

$R^4$ is hydrogen;

n is 0, 1 or 2;

$Ar^1$ is phenyl or phenyl substituted with moieties independently selected from hydrogen, halogen, —S—$C_{1-4}$alkyl, $C_{1-4}$alkyl, $C_{1-4}$alkoxy or $C_{1-4}$alkyl substituted with 1, 2 or 3 halo moieties; and $Ar^2$ phenyl, naphthyl, tetralin, or phenyl, naphthyl or tetralin substituted with moieties independently selected from hydrogen, halogen, cyano, nitro, $C_{1-4}$alkyl, $C_{1-4}$alkoxy or $C_{1-4}$alkyl substituted with 1, 2 or 3 halo moieties.

The invention also encompasses in vivo-hydrolysable precursors and pharmaceutically-acceptable salts of compounds of Formula I, pharmaceutical compositions and formulations containing them, methods of using them to treat diseases and conditions either alone or in combination with other therapeutically-active compounds or substances, processes and intermediates used to prepare them, uses of them as medicaments, uses of them in the manufacture of medicaments and uses of them for diagnostic and analytic purposes.

Compounds of this invention have $NK_1$ antagonist activity and/or SRI activity. Accordingly, this invention comprises such compounds, pharmaceutical compositions containing such compounds and methods of using such compounds to treat central nervous system (CNS) and other disorders.

Compounds of the invention are those in accord with formula I:

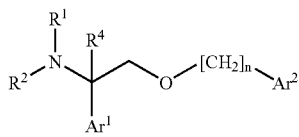

wherein:

R¹ and R² are independently selected from $C_{1-6}$alkyl or $C_{1-6}$alkenyl, or together with the N to which they are bound, form a heterocycle containing 6, 7 or 8 atoms or such a heterocycle substituted with moieties independently selected from hydrogen, halogen, $C_{1-4}$alkyl, $C_{1-4}$alkoxy or $C_{1-4}$alkyl substituted with 1, 2 or 3 halo moieties, amino, or amino substituted with $C_{1-4}$alkyl, $C_{1-4}$alkoxy or $C_{1-4}$alkyl, substituted with 0, 1, 2, or 3 halo moieties;

R⁴ is hydrogen;

n is 0, 1 or 2;

Ar¹ is phenyl or phenyl substituted with moieties independently selected from hydrogen, halogen, —S—$C_{1-4}$alkyl, $C_{1-4}$alkyl, $C_{1-4}$alkoxy or $C_{1-4}$alkyl substituted with 1, 2 or 3 halo moieties; and Ar² phenyl, naphthyl, tetralin, or phenyl, naphthyl or tetralin substituted with moieties independently selected from hydrogen, halogen, cyano, nitro, $C_{1-4}$alkyl, $C_{1-4}$alkoxy or $C_{1-4}$alkyl substituted with 1, 2 or 3 halo moieties;

in vivo-hydrolysable precursors and pharmaceutically-acceptable salts thereof.

Particular compounds of the invention are those of the examples herein.

Another aspect of the invention is pharmaceutically-acceptable salts of a compounds as described herein made with an inorganic or organic acid which affords a physiologically-acceptable anion.

Particular pharmaceutically-acceptable salts of compounds of the invention are those wherein the inorganic or organic acid is selected from hydrochloric, hydrobromic, sulfuric, phosphoric, methanesulfonic, sulfamic, para-toluenesulfonic, acetic, citric, lactic, tartaric, malonic, fumaric, ethanesulfonic, benzenesulfonic, cyclohexylsulfamic, salicyclic and quinic acids.

Another aspect of the invention is a pharmaceutical composition comprising a compound of the invention or an in vivo-hydrolysable precursor or a pharmaceutically-acceptable salt thereof and a pharmaceutically-acceptable carrier.

Yet another aspect of the invention is a method of treating a disease condition wherein antagonism of $NK_1$ receptors and/or SRI activity is beneficial which method comprises administering to a warm-blooded animal an effective amount of a compound of the invention or an in vivo-hydrolysable precursor or a pharmaceutically-acceptable salt thereof.

Still another aspect of the invention is the use of a compound of the invention or an in vivo-hydrolysable precursor or a pharmaceutically-acceptable salt thereof in the preparation of a medicament for use in a disease condition wherein antagonism of the $NK_1$ receptors and/or SRI activity is beneficial.

A further aspect of the invention is a method for treating a disorder or condition selected from hypertension, depression, depression in cancer patients, depression in Parkinson's patients, postmyocardial infarction depression, subsyndromal symptomatic depression, depression in infertile women, pediatric depression, major depression, single episode depression, recurrent depression, child abuse induced depression, post partum depression, generalized anxiety disorder, agoraphobia, social phobia, simple phobias, posttraumatic stress syndrome, avoidant personality disorder, premature ejaculation, anorexia nervosa, bulimia nervosa, obesity, addictions to alcohol, cocaine, heroin, phenobarbital, nicotine or benzodiazepines; cluster headache, migraine, pain, Alzheimer's disease, obsessive-compulsive disorder, panic disorder, dementia, amnestic disorders, age-related cognitive decline, dementia in Parkinson's disease, neuroleptic-induced parkinsonism, tardive dyskinesias, hyperprolactinaemia, vasospasm, cerebral vasculature vasospasm, cerebellar ataxia, gastrointestinal tract disorders, negative symptoms of schizophrenia, premenstrual syndrome, fibromyalgia syndrome, stress incontinence, Tourefte's syndrome, trichotillomania, kleptomania, male impotence, attention deficit hyperactivity disorder, chronic paroxysmal hemicrania and headache associated with vascular disorders in a mammal, wherein antagonism of the $NK_1$ receptors and/or SRI activity is beneficial, comprising administering an effective amount of a compound of the invention or a pharmaceutically-acceptable salt thereof effective in treating such disorder or condition.

In a particular aspect of the invention the method for treating a disorder or condition mentioned herein, comprises administering a compound of the invention in combination with a pharmaceutically-acceptable carrier.

Compounds in accord with formula I and their in vivo-hydrolysable precursors or a pharmaceutically-acceptable salts may be made by processes as described and exemplified herein and by processes similar thereto and by processes known in the chemical art. If not commercially available, starting materials for these processes may be made by procedures which are selected from the chemical art using techniques which are similar or analogous to the synthesis of known compounds.

Pharmaceutically-acceptable salts may be prepared from the corresponding acid in a conventional manner. Non-pharmaceutically-acceptable salts may be useful as intermediates and as such are another aspect of the present invention.

It is well known in the art how to prepare optically-active forms (for example, by resolution of the racemic form or by synthesis from optically-active starting materials) and all optically active forms, enantiomers are compounds of this invention. Further, the mixture of enantiomers can have either or both serotonin and neurokinin activity and/or either of the pure enantiomers can have serotonin and or neurokinin activity.

The following biological test methods, data and Examples serve to illustrate and further describe the invention.

The utility of a compound of the invention or an in vivo-hydrolysable precursor or a pharmaceutically-acceptable salt thereof (hereinafter, collectively referred to as a "Compound") may be demonstrated by standard tests and clinical studies, including those disclosed in the publications described below.

Biological Assays

Test A—SERT Binding Assay

Frozen membrane preparations of a stably transfected HEK293 cell line expressing human 5-HTT receptors were purchased from Receptor Biology (PerkinElmer). Frozen aliquots were rapidly thawed, homogenized, and diluted in assay buffer (AB) containing 50 mM TRIS-HCL, 120 mM NaCl, 5 mM KCl and adjusted to pH 7.4 with NaOH. Final protein concentration was 40 µg/ml. Test compounds were evaluated in competition assays utilizing [$^3$H]-Imipramine Hydrochloride purchased from NEN (PerkinElmer) as the radioligand. The stock radioligand was diluted with AB for a final concentration of approximately 2 nM. Kd for [$^3$H]-Imipramine Hydrochloride was determined to be 2.7 nM. The competition assays were performed on 96-well assay plates—two drugs per plate. Ten serial dilutions (normally 1 µM to 38 pM final concentration) from stock 10 mM solutions of compounds prepared in DMSO. All serial dilutions were made using 20% DMSO. DMSO content in assay is less than 1%. Incubation mixtures were prepared in quadruplicate in 96-well plates (Costar). Final assay volumes per well were 10 µl compound/nonspecific/control (1% DMSO), 20 µl membranes, 20 µl [$^3$H]-Imipramine Hydrochloride, and 150 µl AB. Specific binding was defined by using 10 µM Imipramine. The binding reaction was initiated by adding membranes immediately after adding the radioligand to wells containing buffer plus either test compound, nonspecific, or control. The assay plates were placed on a plate shaker and shaken for thirty min while the reactions reached equilibrium. The plates were then filtered through Beckman GF/B filters, presoaked in 6% PEI, using a Packard Filtermate 196. Filters were washed 5×with 0.2 ml ice-cold wash buffer (5 mM Tris HCl, pH 7.4.) The filters were dried and 35 µl of Microscint20 (Packard) was added to each well. The plates were then counted on a Packard TopCount to determine CPM's per well. Ki values were determined for each test compound utilizing the graphic and analytical software package, GraphPad Prism.

Test B—NK$_1$ FLIPR Assay using Fluo-4 Dye

FLIPR assays are performed with a device marketed by Molecular Devices, Inc., designed to precisely measure cellular fluorescence in a high throughput whole-cell assay. (Schroeder et. al., J. Biomolecular Screening, 1(2), p 75-80, 1996).

Compounds were evaluated for potency in blocking the response of U373 cells to the NK$_1$ receptor agonist Acetyl-[Arg$^6$, Sar$^9$, Met(O$_2$)$^{11}$]-Substance P (ASMSP) using a FLIPR instrument.

U373 cells were loaded with Fluo-4 dye (Molecular Probes) for 45 min at 37° C. and exposed to graded concentrations of compounds for 15 min at room temperature before being challenged with 10 nM-12 nM ASMSP (an approximately EC$_{80}$ concentration). Responses were measured as the peak relative fluorescence after agonist addition. pIC$_{50}$s were calculated from eleven-point concentration-response curves for each compound.

Reagents

| Cell culture medium: | |
|---|---|
| Eagle's MEM with Earle's salts and l-glutamine (500 mL) | Cellgro 10-010-CV |
| Non-essential amino acids, 100× (5 mL) | Cellgro 25-025-CI |
| Sodium pyruvate, 100 mM (5 mL) | Cellgro 25-000-CI |
| L-Glutamine, 200 mM (5 mL) | Cellgro 25-005-CI |
| FBS (50 mL) | Cellgro 35-010-CV |
| Cell harvesting reagents: | |
| DPBS, 1× without Ca$^{++}$ & Mg$^{++}$ | Cellgro 21-031-CV |
| 1× Trypsin -EDTA (0.5% Trypsin, 0.53% EDTA-4Na) | Cellgro 25-052-CI |

| Cell plating medium: | |
|---|---|
| UltraCULTURE | BioWhittaker 12-725F |
| L-Glutamine, 200 mM (5 mL/500 mL) | Cellgro 25-005-CI |
| Working buffer: | |
| 10× Hank's balanced salt solution (100 mL/L) | Gibco 14065-056 |
| HEPES buffer 1 M (15 mL/L, [final] 15 mM) | Cellgro 25-060-CI |
| Probenecid (0.71 g dissolved in 6 mL 1 M NaOH for 1 L, [final] 2.5 mM) DDH$_2$O to 1 L, adjust pH to 7.4 with NaOH | Sigma P-8761 |

Dye solution:
Fluo-4, AM dye, Molecular Probes F-14201. 50 µg lyophilized dye is dissolved in 23 µl DMSO plus 23 µL Pluronic F-127 (Molecular Probes P-3000). The 46 µL of solubilized fluo-4 dye is then added to 10 mL of working buffer solution to provide a working dye concentration of 5 µM. Each 10 mL of diluted dye is sufficient for a 384-well-plate of cells at 25 µL per well.

Agonist:
Acetyl-[Arg$^6$, Sar$^9$, Met(O$_2$)$^{11}$]-Substance P (ASMSP) Stock solution of 3.33×10$^{-2}$ M. Dissolve 100 mg in 3.05 mL DMSO and store in aliquots at 4° C.

Miscellaneous:
DMSO (to dissolve compounds and for tip wash)

Cell Culture and Plating Procedures

U373 cells were grown in cell culture medium described above (30 mL per T-150 flask) and harvested when confluent as follows. Medium was removed by aspiration and cells were washed 1× with 12 mL DPBS, without Ca$^{++}$ and Mg$^{++}$. The DPBS was aspirated and replaced with 3 mL trypsin EDTA. The cells plus trypsin/EDTA were incubated about 2 min at room temperature, until the cells detached from the flask. The harvesting reaction was quenched by addition of 9 mL culture medium and cells were resuspended by trituration.

Cells were passaged at a transfer density of 1:4 every four days. For experiments, cells were counted, pelleted by centrifugation at 400×g for 5 min and resuspended in cell plating medium at a density of 480,000 cells/mL. 25 µL of this cell suspension was added to each well of a black-walled 384-well plate (Falcon Microtest, 35 3962) using a Labsystems Multidrop 384 to give 12,000 cells per well. Plates were incubated at 37° C. overnight (minimum 15 h, maximum 23 h) before use.

Compound and Agonist Preparation

Compounds were dissolved in DMSO at a concentration of 10 mM and 120 µL of these solutions were transferred to the first well (column 1) of each row of a 96-well, round-bottomed, polypropylene storage plate (Costar 3365). Compounds on two such plates were then serially diluted simultaneously in DMSO using a Biomek 2000. 4 µL of each dilution was transferred to a deep well plate (Beckman Coulter 267006) which had been prepared previously to contain 400 µL of freshly made working buffer in each well. Concentrations resulting from this procedure are shown in Table 1. The final compound concentrations in the assay span 11 points, between 10 µM and 0.1 nM, in half-log increments.

The contents of the wells were mixed, and 45 µL of each dilution were transferred—in duplicate—to a 384-well polypropylene compound loading plate (Fisher 12-565-507) so that the 384-well plate contained duplicates of each of the compounds from both 96-well plates over the concentration ranges. Columns 23 and 24 of the plate contain no compound and serve as controls. Wells A-N in columns 23 and 24 were loaded with agonist only and therefore represent the maximal response. Wells O-P in columns 23 and 24 were loaded with only buffer, no agonist, and therefore represent the minimum response.

An ASMSP agonist loading plate was made by taking stock concentration of ASMSP and diluting in working buffer to give a concentration of $3.3 \times 10^{-8}$ M. 45 µL of this solution were transferred to all wells of a 384-well polypropylene agonist loading plate (Fisher 12-565-507) except wells O23, O24, P23 & P24 which contained buffer alone and served as unstimulated controls.

Dye Loading Cells and Adding Compound

For each 384-well assay plate of cells, 10 mL of diluted Fluo-4 dye was prepared as stated above in the methods/reagents section. First, each 384-well cell plate was washed once with working buffer on a CCS Packard plate washer. Any remaining post-wash buffer in the wells was removed by hand and 25 µL per well of Fluo-4 dye was added using a Labsystems Multidrop 384. The cell plate was returned to a 37° C. incubator for 45 min to allow the dye to permeate the cells. After 45 min of dye loading, the cell plates were washed twice with working buffer, leaving a 30 µL volume of buffer in each well. 5 µL of compound dilutions were transferred from the compound plate to the cell plate using a PlateMate. Assay plates were incubated in the presence of compound for 15 min at room temperature in the dark, and then loaded onto FLIPR.

Recording Responses in FLIPR

After the 15 min compound pre-incubation, the plates were loaded onto the FLIPR instrument, 15 µL of ASMSP agonist was added and the cellular response to the agonist was recorded for 90 seconds. The response is measured as the peak relative fluorescence after agonist addition.

Data analysis:

Results contained in the stat files generated by FLIPR were pasted into an Excel analysis template and, after outliers were excluded, $IC_{50}$ values were calculated within the template using XLfit. Individual $IC_{50}$ values were reported, along with $pIC_{50}$. When the two $IC_{50}$'s obtained for a compound differed by more than 3-fold that compound was assayed one or two more times to re-determine the value.

Results:

Ki values obtained in the SERT assay for compounds of the invention ranged from less than 2 nM to about 180 nM. $IC_{50}$ values obtained in the FLIPR assay for compounds of the invention ranged from about 70 nM to about 2 µM.

EXAMPLES

The invention is illustrated by, but not limited to, the following examples in which descriptions, where applicable and unless otherwise stated, the following terms, abbreviations and conditions are used:

aq., aqueous; atm, atmospheric pressure; BOC, 1,1-dimethylethoxycarbonyl, ACN, acetonitrile; DCM, dichloromethane; DMR, N,N-dimethylformamide; DMSO, dimethyl sulfoxide; EtOH, ethanol; Et$_2$O, diethyl ether; EtOAc, ethyl acetate; h, hour(s); HPLC, high performance liquid chromatography; HOBT, 1-hydroxybenzotriazole; MeOH, methanol; min, minutes; MS, mass spectrum; NMR, nuclear magnetic resonance; psi, pounds per square inch; RT, room temperature; sat., saturated; TEA, triethylamine; TFA, trifluoroacetic acid; THF, tetrahydrofuran.

The term "heterocycle" used alone or as a suffix or prefix, refers to a ring structure or molecule of at least three and up to 20 atoms having one or more multivalent heteroatoms, such atoms independently selected from O, N, P or S as part of the ring structure. Heterocycles may be saturated, partially-saturated or unsaturated, may have atoms linked by on or more double bonds and may form one or more rings that may be linked or fused where fused rings share at least two atoms therebetween. Heterocycles may or may not have aromatic character.

Temperatures are given in degrees Celsius (° C.); unless otherwise stated, operations were carried out at room or ambient temperature (18-25° C.).

Organic solutions were dried over anhydrous sodium or magnesium sulfate; evaporation of solvent was carried out using a rotary evaporator under reduced pressure (4.5-30 mm Hg) with a bath temperature of up to 60° C.

Chromatography means flash column chromatography on silica gel unless otherwise noted; solvent mixture compositions are given as volume percentages or volume ratios.

When reported, NMR data is in the form of delta values for major diagnostic protons (given in parts per million (ppm) relative to tetramethylsilane as an internal standard) determined at 300 MHz.

Melting points are uncorrected.

Mass spectra (MS) were obtained using an automated system with atm chemical ionization (APCI) unless otherwise indicated. Masses corresponding to the major isotopic component, or the lowest mass for compounds with multiple masses with nearly equivalent abundance (isotope splitting), are reported.

Where noted that a final compound was converted to the citrate salt, the free base was dissolved in MeOH, DCM, or ACN, combined with citric acid (1.0 equivalents) in MeOH, concentrated under reduced pressure and dried under vacuum (25-60° C.). When indicated that the salt was isolated by filtration from Et$_2$O, the citrate salt of the compound was stirred in Et$_2$O for 4-18 h, recovered by filtration, washed with Et$_2$O, and dried under vacuum (25-60° C.).

Example 1

4-{[2-(3-Chloro-4-fluoroihenyl)-2-piperazin-1-ylethoxy]methyl}-3-methoxy-2-naphthonitrile.

tert-Butyl 4-{1-(3-chloro-4-fluorophenyl)-2-[(3-cyano-2-methoxy-1-naphthyl)methoxy]ethyl}piperazine-1-carboxylate (100 mg, 0.18 mmol) was dissolved in DCM (2 mL) and TFA (2 mL) was added. After 2 h the volatiles were removed under reduced pressure. The residue was taken up in EtOAc (20 mL) and washed with sat. aq. NaHCO$_3$ (20 mL). The organic phase was dried over Na$_2$SO$_4$, filtered through a pad of diatomaceous earth and the volatiles removed under reduce pressure. Chromatography of the residue on SiO$_2$ (0-5% 2 M NH$_3$ in MeOH:DCM) afforded the title compound as an off-white solid (81.6 mg, 79%). The citrate salt was formed by the addition of citric acid (1.0 equivalents) to a methanolic solution of the title compound. Concentration under reduced pressure afforded the desired salt form of the product as an off-white powder. MS m/z 454.4 (M+H)$^+$. $^1$H NMR (300.1 MHz, DMSO+TFA) δ8.64(s, 1H), 8.08(t, J=7.6 Hz, 2H), 7.80(dd, J=1.9, 7.1 Hz, 1H), 7.72(t, J=7.1 Hz, 1H), 7.64(t, J=7.6 Hz, 1H), 7.55-7.45 (m, 2H),5.06 (dd, J=15.4, 11.0 Hz, 2H), 4.78(t, J=5.0 Hz, 1H), 4.20(d, J=5.0 Hz, 2H), 3.99 (s, 3H), 3.41-3.34 (m, 6H), 3.23-3.19 (m, 2H), 2.75 (dd, J=33.0, 15.4 Hz, 4H), 1.83 (s, 1H).

The requisite tert-butyl 4-{1-(3-chloro-4-fluorophenyl)-2-[(3-cyano-2-methoxy-1-naphthyl)methoxy]ethyl}piperazine-1-carboxylate was synthesized using the following method. tert-Butyl 4-[1-(3-chloro-4-fluorophenyl)-2-hydroxyethyl]piperazine-1-carboxylate (65 mg, 0.18 mmol) was dissolved in THF (1.8 mL). 4-(Iodomethyl)-3-methoxy-2-naphthonitrile (70 mg, 0.22 mmol) was added followed by NaH (9 mg, 0.36 mmol). After reacting at RT overnight, water (60 mL) was added. The mixture was extracted with EtOAc (40 mL). The organic phase was dried over Na$_2$SO$_4$, filtered through a pad of diatomaceous earth and the volatiles removed under reduce pressure. Chromatography of the residue on SiO$_2$ (0-30% EtOAc:hexane) afforded the title compound (99 mg). MS m/z 554.6 (M+H)$^+$. The requisite tert-butyl 4-[1-(3-chloro-4-fluorophenyl)-2-hydroxyethyl]piperazine-1-carboxylate was synthesized using the following method.

Borane-methyl sulfide complex (2M in THF, 1.07 mL) was added to a solution of [4-(tert-butoxycarbonyl)piperazin-1-yl](3-chloro-4-fluorophenyl)acetic acid (200 mg, 0.54 mmol) in THF (3 mL). After 30 min at RT the reaction was heated to reflux for 4 h. After cooling the reaction to RT, MeOH (10 ml) was slowly added. After stirring overnight the volatiles were removed under reduced pressure. Chromatography of the residue on SiO$_2$ (0-50% EtOAc:hexane) afforded the title compound (160 mg, 83%). MS m/z 359.3 (M+H)$^+$, 303.2 (M+H-t-butyl).

The requisite [4-(tert-butoxycarbonyl)piperazin-1-yl](3-chloro-4-fluorophenyl)acetic acid was synthesized using the following method. (3-Chloro-4-fluorophenyl)boronic acid (440 mg, 2.52 mmol), tert-butyl piperazine-1-carboxylate (469 mg, 2.52 mmol) and glyoxylic acid monohydrate (232 mg, 2.52 mmol) were reacted together in DCM (10 mL) at reflux overnight. The volatiles were removed under reduced pressure. Chromatography of the residue on SiO$_2$ (0-10% MeOH:DCM) afforded the title compound (767 mg, 82%). MS m/z 373.1 (M+H)$^+$, 317.1 (M+H-t-butyl). $^1$H NMR (300.1 MHz, DMSO) δ12.80 (s, 0.6H), 7.59(d, J=7.2 Hz, 1H), 7.42 (d, J=7.2 Hz, 2H), 4.09(s, 1H), 3.30 (s, 2H), 3.16 (s, 2H), 2.35 (m, 4H), 1.38 (s, 9H).

Examples 2-28

The compounds shown in the following table were prepared in a manner analogous to that described in Example 1:

| Ex. No. | | Name | MW | MS m/z (M + H)+ |
|---|---|---|---|---|
| 1 | 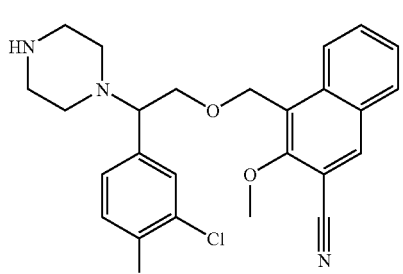 | 4-{[2-(3,chloro-4-fluorophenyl)-2-piperazin-1-ylethoxy]methyl}-3-methoxy-2-naphthonitrile | | 454.4 |
| 2 | 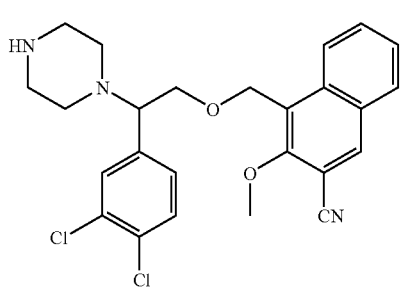 | 4-}]2-(3,4-dichlorophenyl)-2-piperazin-1-ylethoxy]methyl}-3-methoxy-2-naphthonitrile | 470.40 | 470.2, 472.2 |
| 3 | 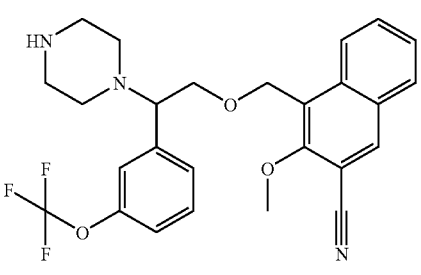 | 3-methoxy-4-({2-piperazin-1-yl-2-[3-(trifluoromethyl)phenyl]ethoxy}methyl)-2-naphthonitrile | 485.51 | 486.4 |

-continued

| Ex. No. | | Name | MW | MS m/z (M + H)+ |
|---|---|---|---|---|
| 4 | 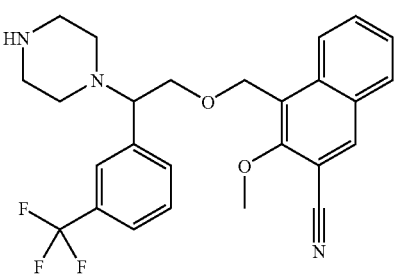 | 3-methoxy-4-({2-piperazin-1-yl--2[3-(trifluoromethyl)-phenyl]ethoxy}methyl)-2-naphthonitrile | 469.51 | 470.5 |
| 5 | 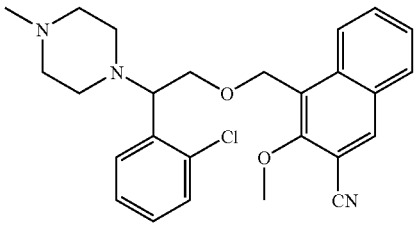 | 4-{[2-(2-chlorophenyl)-2-(4-methylpiperazin-1-yl)ethoxy]methyl}-3-methoxy-2-naphthonitrile | 449.98 | 450.2 |
| 6 | 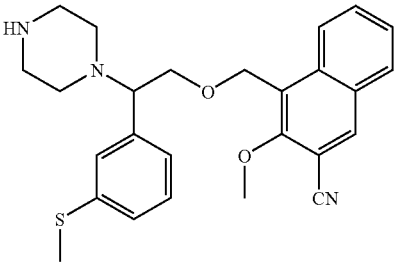 | 3-methoxy-4-({2-[3-(methoxylthio)phenyl]-2-piperazin-1-ylethoxy}methyl)-2-naphthonitrile | 447.60 | 448.5 |
| 7 | 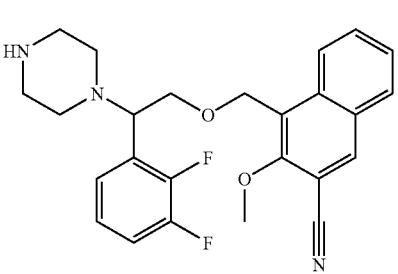 | 4-{[2-(2,3-difluorophenyl)-2-piperazin-1-ylethoxy]methyl}-3-methoxy-2-naphthonitrile | 437.49 | 438.4 |
| 8 | 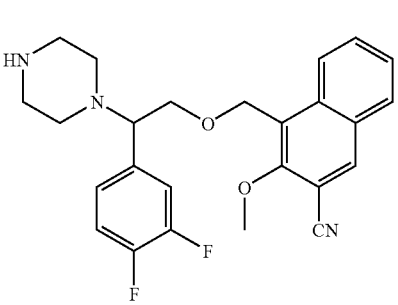 | 4-{[2-(3,4-difluorophenyl)-2-piperazin-1-ylethoxy]methyl}-3-methoxy-2-naphthonitrile | 437.49 | 438.2 |

| Ex. No. | | Name | MW | MS m/z (M + H)+ |
|---|---|---|---|---|
| 9 | 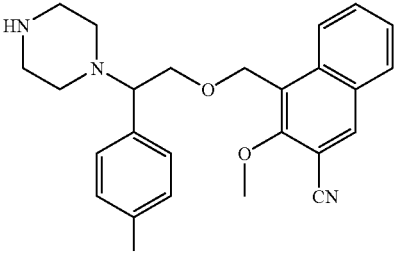 | 4-{[2-(4-chlorophenyl)-2-piperazin-1-ylethoxy]methyl}-3-methoxy-2-naphthonitrile | 435.96 | 436.4 |
| 10 | 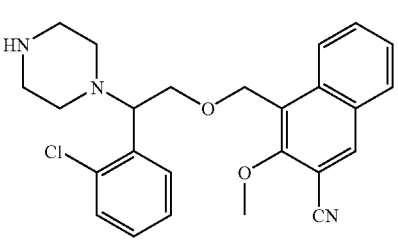 | 4-{[2-(2-chlorophenyl)-2-piperazin-1-ylethoxy]methyl}-3-methoxy-2-naphthonitrile | 435.96 | 436.3 |
| 11 | 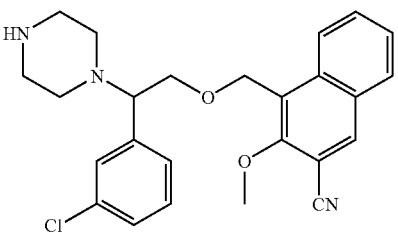 | 4-{[2-(3-chlorophenyl)-2-piperazin-1-ylethoxy]methyl}-3-methoxy-2-naphthonitrile | 435.96 | 436.2 |
| 12 | 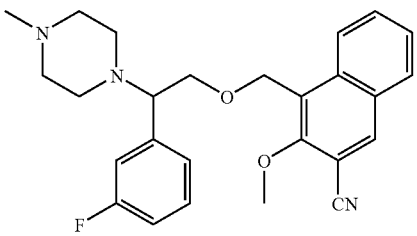 | 4-{[2-(3-fluorophenyl)-2-(4-methylpiperazin-1-yl)ethoxy]methyl}-3-methoxy-2-naplithonitrile | 433.53 | 434.6 |
| 13 | 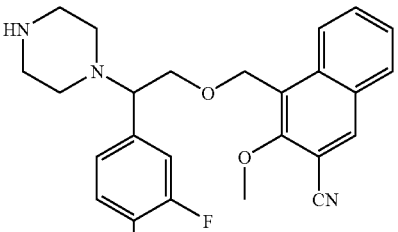 | 4-{[2-(3-fluoro-4-methylphenyl)-2-piperazin-1-ylethoxy]methyl}-3-methoxy-2-naplithonitrile | 433.53 | 434.5 |
| 14 | 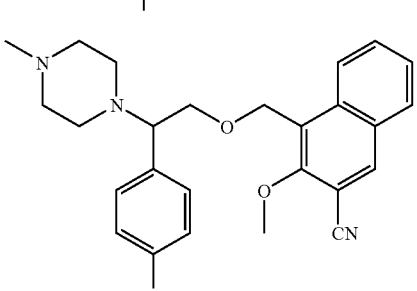 | 4-{[2-(4-fluorophenyl)-2-(4-methylpiperazin-1-yl)ethoxy]methyl}-3-methoxy-2-naplithonitrile | 433.53 | 434.5 |

-continued

| Ex. No. | | Name | MW | MS m/z (M + H)+ |
|---|---|---|---|---|
| 15 | 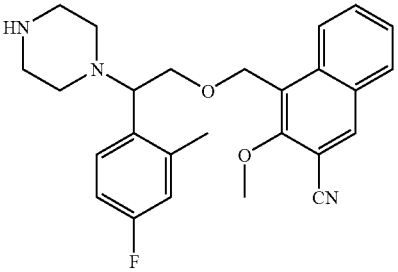 | 4-{[2-(4-fluoro-2-methylphenyl)-2-piperazin-1-ylethoxy]methyl}-3-methoxy-2-naphthonitrile | 433.53 | 434.5 |
| 16 | 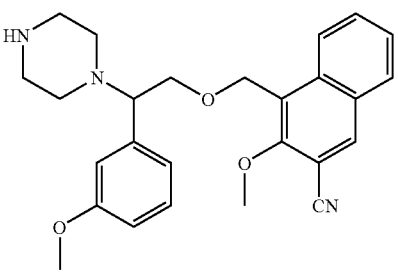 | 3-methoxy-4-{[2-(3-methoxyphenyl)-2-piperazin-1-ylethoxy]methyl}-2-naplithonitrile | 431.54 | 432.6 |
| 17 | 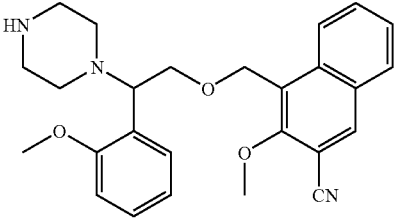 | 3-methoxy-4-{[2-(2-methoxyphenyl)-2-piperazin-1-ylethoxy]methyl}-2-naphthonitrile | 431.54 | 432.6 |
| 18 | 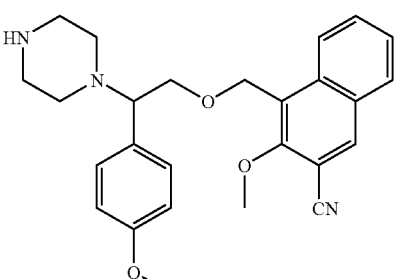 | 3-methoxy-4-{[2-(4-methoxyphenyl)-2-piperazin-1-ylethoxy]methyl}-2-naplithonitrile | 431.54 | 432.5 |
| 19 | 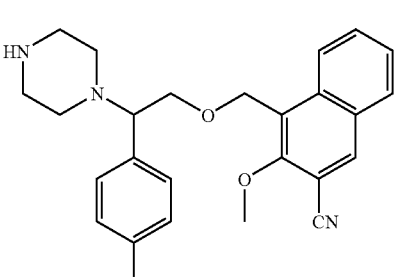 | 4-{[2-(4-fluorophenyl)-2-piperazin-1-ylethoxy]methyl}-3-methoxy-2-naphthonitrile | 419.50 | 420.3 |

-continued

| Ex. No. | | Name | MW | MS m/z (M + H)+ |
|---|---|---|---|---|
| 20 | 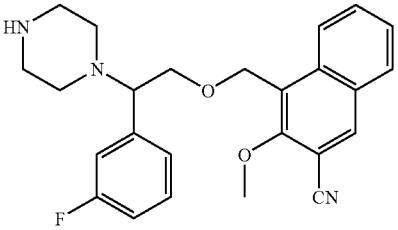 | 4-{[2-(3-fluorophenyl)-2-piperazin-1-ylethoxy]methyl}-3-methoxy-2-naphthonitrile | 419.50 | 420.3 |
| 21 | 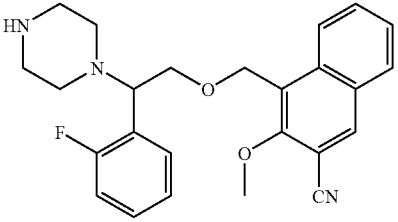 | 4-{[2-(2-fluorophenyl)-2-piperazin-1-ylethoxy]methyl}-3-methoxy-2-naphthonitrile | 419.50 | 420.3 |
| 22 | 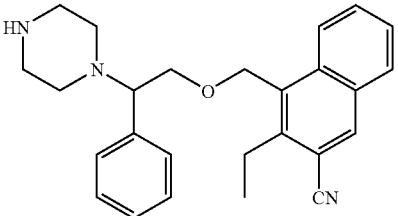 | 3-ethyl-4-{[2-(4-fluorophenyl)-2-piperazin-1-ylethoxy]methyl}-2-naphthonitrile | 417.53 | 418.3 |
| 23 | 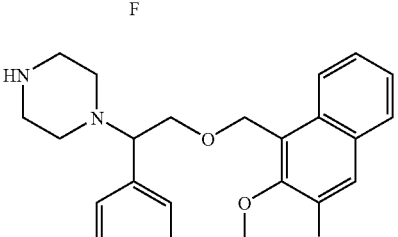 | 3-methoxy-4-{[2-(4-methylphenyl)-2-piperazin-1-ylethoxy]methyl}-2-naphthonitrile | 415.54 | 416.5 |
| 24 | 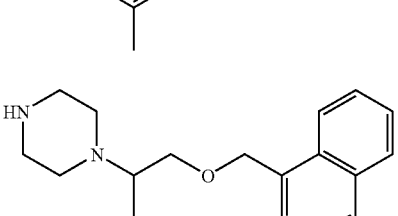 | 3-methoxy-4-{[2-(3-methylphenyl)-2-piperazin-1-ylethoxy]methyl}-2-naplithonitrile | 415.54 | 416.5 |
| 25 | 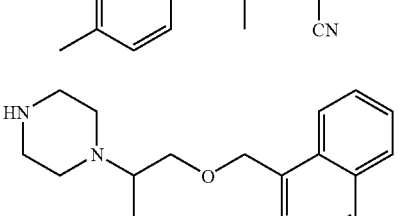 | 3-methoxy-4-[(2-phenyl-2-piperazin-1-ylethoxy)methyl]-2-naphthonitrile | 401.51 | 402.5 |

-continued

| Ex. No. | Name | MW | MS m/z (M + H)+ |
|---|---|---|---|
| 26 | 4-{[2-(4-fluorophenyl)-2-piperazin-1-ylethoxy]methyl}-2-naphthonitrile | 389.48 | 390.3 |
| 27 | 1-[2-[(4-fluoro-1-naphthyl)methoxy]-1-(4-fluorophenyl)ethyl]piperazine | 382.45 | 383.2 |
| 28 | 1-[2-[(3-bromo-2-methoxy-5,6,7,8-tetrahydronaphthalen-1-yl)methoxy]-1-(4-fluorophenyl)ethyl]piperazine | 477.42 | 477.2, 479.2 |

What is claimed is:

1. A compound according to structural diagram I:

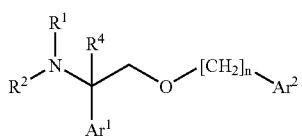

wherein:

$R^1$ and $R^2$ are independently selected from $C_{1-6}$alkyl or $C_{1-6}$alkenyl, or together with the N to which they are bound, form a heterocycle containing 6, 7 or 8 atoms or such a heterocycle substituted with moieties independently selected from hydrogen, halogen, $C_{1-4}$alkyl, $C_{1-4}$alkoxy, and $C_{1-4}$alkyl substituted with 1, 2 or 3 halo or amino; wherein said amino is optionally substituted with $C_{1-4}$alkyl, $C_{1-4}$alkoxy or $C_{1-4}$alkyl substituted with 1, 2, or 3 halo;

$R^4$ is hydrogen;

n is 0, 1 or 2;

$Ar^1$ is phenyl or phenyl substituted with moieties independently selected from hydrogen, halogen, —S—$C_{1-4}$alkyl, $C_{1-4}$alkyl, $C_{1-4}$alkoxy and $C_{1-4}$alkyl substituted with 1, 2 or 3 halo; and $Ar^2$ is naphthyl or tetralin, or naphthyl or tetralin substituted with moieties independently selected from hydrogen, halogen, cyano, nitro, $C_{1-4}$alkoxy, and $C_{1-4}$alkyl substituted with 1, 2 or 3 halo moieties;

or an in vivo hydrolysable precursor or a pharmaceutically-acceptable salt thereof.

2. A pharmaceutically-acceptable salt of a compound according to claim 1 made with an inorganic or organic acid which affords a physiologically-acceptable anion.

3. A pharmaceutically-acceptable salt of a compound according to claim 2, wherein said inorganic or organic acid is selected from hydrochloric, hydrobromic, sulfuric, phosphoric, methanesulfonic, sulfamic, para-toluenesulfonic, acetic, citric, lactic, tartaric, malonic, fumaric, ethanesulfonic, benzenesulfonic, cyclohexylsulfamic, salicyclic and quinic acids.

4. A pharmaceutical composition comprising a compound according to claim 1, an in vivo-hydrolysable precursor or a pharmaceutically-acceptable salt thereof and a pharmaceutically-acceptable carrier.

5. A method for treating a disorder or condition selected from hypertension, depression in cancer patients, depression in Parkinson's patients, postmyocardial infarction depression, subsyndromal symptomatic depression, depression in infertile women, pediatric depression, major depression, single episode depression, recurrent depression, child abuse induced depression, post partum depression, generalized anxiety disorder, agoraphobia, social phobia, simple phobias, posttraumatic stress syndrome, avoidant personality disorder, premature ejaculation, anorexia nervosa, bulimia nervosa, obesity, addictions to alcohol, cocaine, heroin, phenobarbital, nicotine or benzodiazepines; cluster headache, migraine, pain, Alzheimer's disease, obsessive-compulsive disorder, panic disorder, dementia, amnestic disorders, age-related cognitive decline, dementia in Parkinson's disease, neuroleptic-induced parkinsonism, tardive dyskinesias, hyperprolactinaemia, vasospasm, cerebral vasculature vasospasm, cerebellar ataxia, gastrointestinal tract disorders, negative symptoms of schizophrenia, premenstrual syndrome, fibromyalgia syndrome, stress incontinence, Tourette's syndrome, trichotillomania, kleptomania, male impotence, attention deficit hyperactivity disorder, chronic paroxysmal hemicrania and headache associated with vascular disorders in a mammal, comprising administering an effective amount of a compound according to claim 1 or a pharmaceutically-acceptable salt thereof effective in treating such disorder or condition.

6. The method according to claim 5, wherein said compound is administered in combination with a pharmaceutically-acceptable carrier.

7. A compound according to structural diagram I:

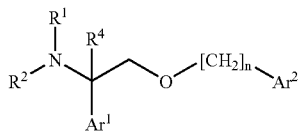

I wherein:

$R^1$ and $R^2$, together with the N to which they are bound, form a heterocycle containing 6, 7 or 8 atoms; wherein said heterocycle is optionally substituted with a moiety independently selected from hydrogen, halogen, $C_{1-4}$alkyl, $C_{1-4}$alkoxy, and $C_{1-4}$alkyl substituted with 1, 2 or 3 halo or amino; wherein said amino is optionally substituted with $C_{1-4}$alkyl, $C_{1-4}$alkoxy, or $C_{1-4}$alkyl substituted with 1, 2, or 3 halo;

$R^4$ is hydrogen;

n is 1 or 2;

$Ar^1$ is phenyl optionally substituted with a moiety independently selected from hydrogen, halogen, —S—$C_{1-4}$alkyl, $C_{1-4}$alkyl, $C_{1-4}$alkoxy, and $C_{1-4}$alkyl substituted with 1, 2, or 3 halo; and $Ar^2$ is naphthyl optionally substituted with a moiety independently selected from hydrogen, halogen, cyano, nitro, $C_{1-4}$alkyl, $C_{1-4}$alkoxy, and $C_{1-4}$alkyl substituted with 1, 2, or 3 halo;

or a pharmaceutically-acceptable salt thereof.

8. A pharmaceutically-acceptable salt of a compound according to claim 7 made with an inorganic or organic acid which affords a physiologically-acceptable anion.

9. A pharmaceutically-acceptable salt of a compound according to claim 8 wherein said inorganic or organic acid is selected from hydrochloric, hydrobromic, sulfuric, phosphoric, methanesulfonic, sulfamic, para-toluenesulfonic, acetic, citric, lactic, tartaric, malonic, fumaric, ethanesulfonic, benzenesulfonic, cyclohexylsulfamic, salicyclic, and quinic acids.

10. A pharmaceutical composition comprising a compound according to claim 7, or a pharmaceutically-acceptable salt thereof, and a pharmaceutically-acceptable carrier.

* * * * *